United States Patent
Arlettaz et al.

(10) Patent No.: US 8,628,538 B2
(45) Date of Patent: Jan. 14, 2014

(54) DEVICE FOR POSITIONING AND ADJUSTING A VIEWING AXIS

(75) Inventors: Yvan Arlettaz, Monthey (CH); Christian Bonjour, Begnins (CH)

(73) Assignee: Chirmat SA, Monthey (CH)

( * ) Notice: Subject to any disclaimer, the term of this patent is extended or adjusted under 35 U.S.C. 154(b) by 0 days.

(21) Appl. No.: 13/457,038

(22) Filed: Apr. 26, 2012

(65) Prior Publication Data
US 2012/0253354 A1   Oct. 4, 2012

Related U.S. Application Data
(63) Continuation of application No. PCT/EP2009/064234, filed on Oct. 28, 2009.

(51) Int. Cl.
- *A61B 17/58*   (2006.01)
- *A61B 17/60*   (2006.01)
- *A61F 2/00*   (2006.01)

(52) U.S. Cl.
USPC ............................................ 606/104; 606/98

(58) Field of Classification Search
USPC ................................................... 606/98, 104
See application file for complete search history.

(56) References Cited

U.S. PATENT DOCUMENTS

| | | |
|---|---|---|
| 4,621,628 A | 11/1986 | Brudermann |
| 4,865,025 A | 9/1989 | Buzzi et al. |
| 5,049,051 A | 9/1991 | Keleher |
| 5,411,503 A | 5/1995 | Hollstien et al. |
| 5,514,145 A | 5/1996 | Durham et al. |
| 6,162,228 A | 12/2000 | Durham |
| 2006/0015101 A1 | 1/2006 | Warburton et al. |

FOREIGN PATENT DOCUMENTS

| | | |
|---|---|---|
| EP | 0187283 A1 | 7/1986 |
| WO | WO-9814121 A1 | 4/1998 |
| WO | WO-2008017501 A1 | 2/2008 |
| WO | WO-2009109371 A2 | 9/2009 |

*Primary Examiner* — Sameh Boles
(74) *Attorney, Agent, or Firm* — Blank Rome LLP

(57) ABSTRACT

Method for positioning a viewing axis in relation to a distal fixation hole (2) for an intramedullary nail (1). A rigid support (3) is fixed to the proximal end of the nail (1). An adjustable viewing device (9) is mounted on the rigid support (3). A coarse adjustment is done of the length of the rigid support according to the length of the nail (1). A coarse adjustment is done in order to move the viewing device (9) closer to the nail, taking account of the patient's build. A precise adjustment is done of the position of the viewing device in relation to the nail, involving the translational and/or rotational movement of the viewing device in a plane perpendicular to the longitudinal axis of the viewing device (Z).

17 Claims, 6 Drawing Sheets

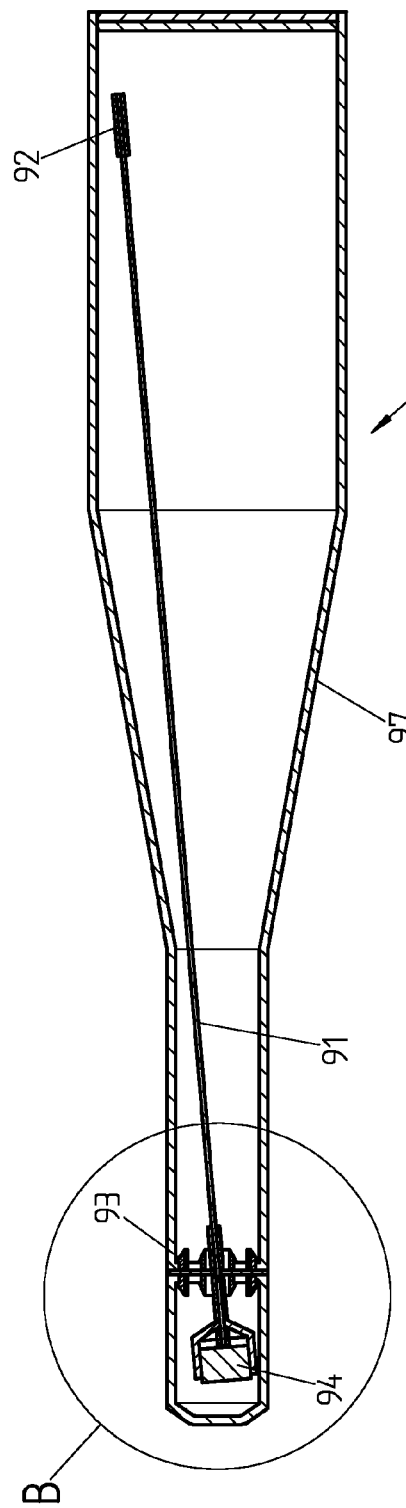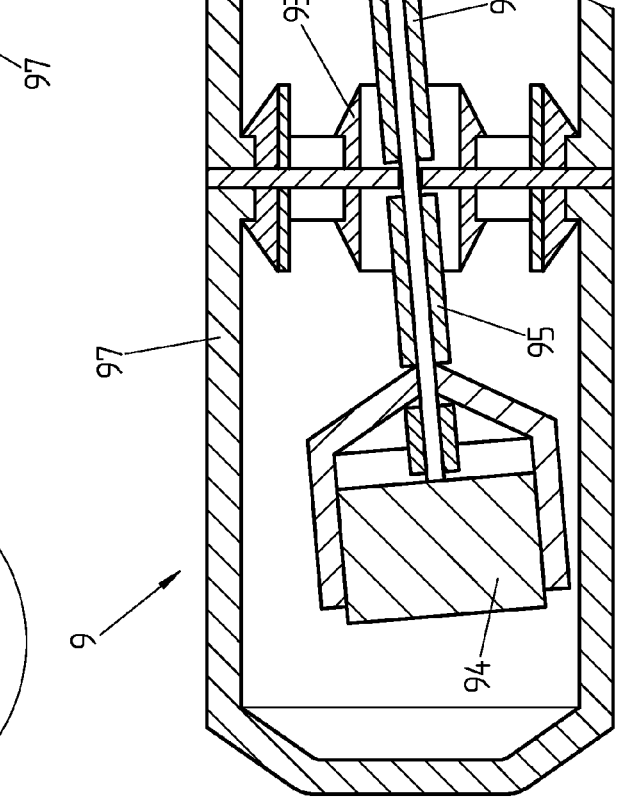

DEVICE FOR POSITIONING AND ADJUSTING A VIEWING AXIS

RELATED APPLICATIONS

This application is a continuation of international application PCT/EP2009/064234 filed on Oct. 28, 2009, the contents of which is hereby incorporated by reference.

TECHNICAL FIELD

The present invention concerns an improvement to devices for positioning a viewing axis, notably for localizing a distal hole in an intramedullary nail for the surgical treatment of fractures of long bones.

STATE OF THE ART

Centromedullary nails are used in the field of surgery for stabilizing fractures of long bones. This type of nail is inserted in long bones, for example the femur, having central cavities in which they can be lodged by simply drilling the longitudinal extremities of the bone.

When a surgeon wishes to introduce an intramedullary nail into a long bone, for example a femur, he first pierces a longitudinal extremity thereof, generally at the level of the buttocks, and then drives the nail into the bone's central cavity. In order to prevent torsional movements of this intramedullary nail thus positioned, these nails contain fixation holes at their proximal and distal extremities, in which screws or pins must be introduced transversally in order to suppress these undesirable torsional movements to ensure a rapid recovery process. The main difficulty for the surgeons in determining the position and the axis of the distal fixation hole arises from the uncertainty associated with the deformation to which the nail is subjected when it is introduced into the bone, since the nail obviously has elastic properties in order for it to be able to follow the trajectory of the bone's cavity.

The orthopedic surgeon must on the one hand localize the location of the hole and, on the other hand, determine the axis of the hole during the necessary drilling of the bone before introducing the screw or the pin. The localization and direction of drilling depend on the deformation sustained by the nail to follow the shape of the bone's cavity. It is thus necessary to find again the position and the orientation of the hole after the nail has been introduced into the bone.

Many systems exist to help the surgeons during this operation and assist them during drilling. Traditionally, the position of the nail is determined by exposition to x-rays, which however requires a complex infrastructure which is not available everywhere.

Electronic apparatus are often involved for visualizing the viewing coordinates, such as for example in U.S. Pat. No. 4,621,628 or even in U.S. Pat. No. 5,411,503. These electronic apparatus require the presence of a source of current that is not always available. Such apparatus require the complexity inherent to their use to be mastered and thus an appropriate training. They furthermore often prove very expensive.

Solutions involving magnets have appeared to make possible an adjustment that requires less electronic equipment for the display, signal processing and connection, and which thus reduces the operating costs. U.S. Pat. No. 5,049,051 and U.S. Pat. No. 5,514,145 describe for example a system implementing one or several magnets inside the intramedullary nail and which work with a viewing system in order to accurately localize the hole before drilling. These methods using essentially mechanical viewing apparatus do not however guarantee optimum accuracy, notably as regards the alignment of the drilling axis relative to the hole.

In most cases, the drill is coupled with a viewing system based on a pivoting magnet that determines a drilling axis that can be adjusted according to 6 degrees of freedom. The magnet does indeed allow the hole's position to be localized accurately, but as its field lines are omnidirectional and isotropic, they do not indicate the direction of the hole's axis. Thus, the drilling angle can be oblique relative to the hole's axis without this system being able to either indicate it or correct it.

Various documents describe supports that enable the viewing and drilling system to be integrally united in relation to the nail. U.S. Pat. No. 6,162,228 and WO9814121 describe such U-shaped supports, with one rail essentially parallel to the intramedullary nail. The support makes it possible to orient the viewing device, which can pivot in order be oriented according to the axis of the fixation hole traversing the nail.

These devices will indeed make it possible to avoid an oblique drilling, but are not of any help when the hole is not at the expected location in the plane.

Furthermore, U.S. Pat. No. 6,162,228 requires a magnet to be oriented correctly inside the nail in order to position its poles relative to the axis of the fixation hole. It is difficult to position a removable magnet correctly inside a deformed nail.

Such a rotational adjustment furthermore does not allow the viewing axis to be adapted in a satisfactory manner when the intramedullary nail is curved according to the shape of the patient's bone, notably when this deformation occurs in a plane perpendicular to the axis of the fixation hole.

Furthermore, U.S. Pat. No. 6,162,228 uses an electronic compass to generate a visual or acoustic signal. The manufacturing costs of such a compass prove high; this device is furthermore difficult to sterilize for repeated use.

Many devices of the prior art enable the position and the orientation of the viewing device and of the drill to be adjusted according to a large number of degrees of freedom. The orthopedic surgeon thus has many possibilities for adjusting the device in order to find the appropriate position and orientation. This results in a considerable adjustment time, which unnecessarily increases the duration of the operation and complicates rehabilitation.

Other devices on the other hand have adjustment possibilities that are too limited and do not allow a precise adjustment of the orientation or of the position. This frequently results in the necessity for the orthopedic surgeon to make a hole in the bone that is not perfectly aligned with the hole through the nail. The screw or pin is then difficult to insert and the surgeon must make an incision unnecessarily large and difficult to heal to allow this screw or pin to be inserted.

BRIEF DESCRIPTION OF THE INVENTION

The aim of the present invention is to propose a device positioning and aligning a viewing axis relative to a distal fixation hole of an intramedullary nail that is free from the limitations known from the prior art.

One aim is also to propose a device for positioning and aligning a viewing axis relative to a distal fixation hole that enables the surgeon to determine accurately the position and the orientation of the hole with a minimum of adjustments, according to a limited number of degrees of freedom.

The invention is based on the observation that long bones, notably the femur, of different individuals have a shape that vary little. Deformations of the nail inside the medullary cavity of the bone are thus predictable, so that the position and orientation of the distal fixation hole can be found again accurately and with a limited number of adjustments according to a limited number of degrees of freedom.

The invention is based in particular on the observation that adjustments in a single plane perpendicular to the axis of the viewing device/of the drill are sufficient to align the drilling axis with the distal hole through the intramedullary nail.

The invention is also based on the observation that the orientation of the axis of the distal hole changes little even when the nail becomes deformed. The changes of orientation due notably to the nail's curvature are limited and do not prevent the drilling nor the insertion of a screw or a pin taking into account the existing play. It is thus not necessary to provide an adjustment of the inclination of the viewing device's axis; such an adjustment option is even detrimental since it makes the adjustment more complex and slower.

It is thus possible to make a support that enables a precise adjustment of the viewing device and of the drill according to the most relevant degree or degrees of freedom and to block the translational or rotational movements according to all the other degrees of freedom. In a preferred embodiment, the viewing device and the drill can thus move only by translational and/or rotational movements in a plane perpendicular to the longitudinal axis of the hole in the undeformed nail; the support prevents all other displacements relative to the nail. One thus capitalizes on the a priori knowledge of the theoretical position and orientation of the hole.

In a first embodiment, the precise adjustments are made according to a single degree of freedom, by a translational movement of the viewing device in a plane perpendicular to the viewing and drilling axis, and along a translational direction perpendicular to the axis of the undeformed nail. This embodiment has the advantage of a very simple execution, since the device requires only a precise adjustment means along a single axis, which is moreover linear. This variant is thus both economical and easy to use.

In a second embodiment, the adjustments are made by a rotational movement in the plane described here above and around an axis parallel to the viewing and drilling axis. This variant is also economical and easy to use; it furthermore has the advantage of adapting to greater deformations of the nail.

A degree of precise adjustment by a translational movement of the viewing device parallel to the nail's axis can be provided. This variant increases the cost of the device and makes the adjustment more complex, but provides maximum flexibility and enables the viewing device and the nail's hole to be aligned accurately even in the case of a considerable flexion or deformation of the nail.

The device thus enables the viewing device to be aligned with the axis of the nail's distal hole only by displacements along one or even two degrees of freedom in a single plane. These displacements are particularly intuitive for the orthopedic surgeon and their effect on the position of the pointer in the viewing device is much easier to predict that in the case of displacements along other degrees of freedom in three dimensions. This results in a shorter adjustment time and length of the operation.

A precise or fine adjustment in the present application means continuous adjustments, depending on indications given in the viewing device, in order to adapt the position and the orientation of the viewing device depending on the deformations of the medullary nail.

A priori adjustments of the device according to a greater number of degrees of freedom are still possible, notably in order to adapt in advance the length of the device to different nail lengths or to minimize the distance between the nail and the viewing device depending on the patient's build. These preliminary adjustments do not however constitute precise or fine adjustments and are not made according to indications in the viewing device.

The invention thus pertains to different embodiments of a device for positioning a viewing axis, comprising a magnetic viewing device and wherein the only precise or fine adjustments possible that influence the indications of the viewing device are made according to one or at most two degrees of freedom in a plane perpendicular to the axis of the viewing device and of the hole in the undeformed nail. The other adjustments that may remain possible are either coarse adjustments (for example adjustments that are not performed in a continuous manner) generally made upon installation and independently of the indications of the viewing device, or adjustments without significant influence on the indications in the viewing device (for example to move the viewing device closer to the bone).

BRIEF DESCRIPTION OF THE FIGURES

Examples of embodiments of the invention are given in the description illustrated by the attached figures, in which:

FIG. 5 is a cross-sectional view of the magnetic viewing device of the invention.

FIG. 6 is a cross-sectional view of a detail of the magnetic viewing device of the invention.

EXAMPLE(S) OF EMBODIMENTS OF THE INVENTION

Figure 1:
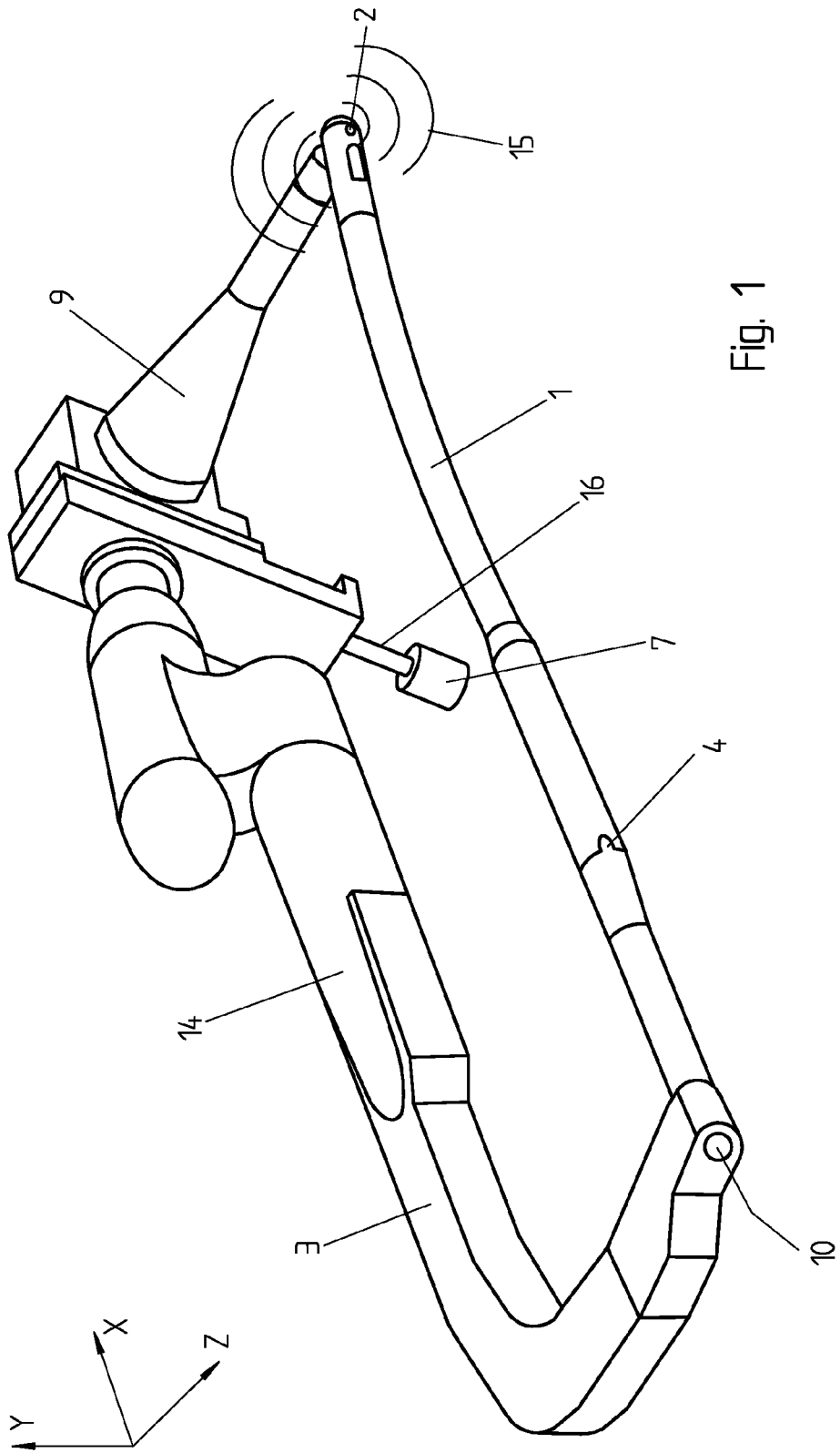
FIG. 1 illustrates in perspective a device according to a first embodiment of the invention.

FIG. 1 is a perspective view of a viewing device according to a first embodiment of the invention. The axis X corresponds to the longitudinal axis of the undeformed nail 1 and the axis Z (viewing axis) corresponds to the axis of the viewing device 9 and of the undeformed distal fixation hole 2 (the hole). The rigid support 3 makes it possible to position the viewing device 9 relative to the nail. The reference number 4 indicates a shape-keyed connection 4 where the support 3 is fastened onto the nail 1.

A removable sleeve 14 allows the length of the rigid support 3 to be adapted depending on the length of nail used; this is not a precise or fine adjustment but only a possibility of adapting to nails of different standard lengths, typically by increments of several centimeters. In one embodiment, the length of the rigid support can be modified by selecting an assembly part, such as the sleeve 14 of FIG. 1, depending on the length of the nail 1.

The viewing device 9 can be moved closer to or further apart from the bone by a Z-shaped translation movement in order to reduce the distance between the viewing device and the magnet in the nail. This is however not a precise or fine adjustment to center the viewing device, but rather an adaptation made a priori to take account of the patient's build. This adjustment can be done in advance independently of the indications in the viewing device 9. Even during this adjustment, the orientation of the viewing device does not change in relation to the nail. The displacements of the viewing device along its longitudinal axis Z thus only allow the interaction between the magnet of the nail and the magnet of the viewing device to be improved by moving them closer together. To all intents and purposes, these movements closer together along the axis Z will however practically not influence the indications displayed by the viewing device.

The nail 1 is preferably hollow to allow it to deform in the bone and for a magnet to be introduced into it to serve as a target for the viewing inwards, by selecting one of the distal locking holes, for example the distal fixation hole 2. The longitudinal channel 10 enables a rod, not represented, bearing for example a magnet or a ferromagnetic element at its extremity, to be inserted. The field lines 15 of the magnet, which will enable the viewing to be oriented, can be distinguished.

In this embodiment, the precise or fine adjustment of the position of the viewing device 9 is made by means of the adjustment knob 7 that enables the viewing device to be displaced along the axis Y in relation to the nail 1. During the adjustment, the viewing device 9 thus moves relative to the nail only by translation movements along the rectilinear axis Y in a plane perpendicular to the axis Z of the viewing device 9 and of the hole 2. The other degrees of freedom are blocked. The orthopedic surgeon thus only needs to actuate the knob 7 to displace the viewing device 9 along the axis Y and in order to achieve the best possible alignment in the viewing device.

The adjustment along the axis Y must be very fine because the play for positioning the screw or the pin in the distal fixation hole 2 is only on the order of the millimeter. It is furthermore necessary to prevent mis-adjustments during the replacement of the viewing device by the drill. In one embodiment, a threaded rod 16 integrally united of the knob 7 turns with it; the other extremity of this rod is engaged in a threaded hole (not represented) integrally united with the viewing device 9. A spring (not represented) maintains a compression along the adjustment axis Y on the viewing device 9, so that the viewing device 9 is engaged in a sliding displacement along Y when the rod 16 turns with the knob 7. The compression exerted by the spring enables the friction forces to be increased to hold the knob 7 in an adjustment position whilst still enabling a precise or fine adjustment along this axis. It is also possible to provide the axis of the knob with a worm screw meshing with a rack integrally united with the viewing device.

Tests and studies have shown that this Y adjustment is sufficient to adjust the axis of the viewing device 9 with the axis of the hole 2 in the nail 1 with a remarkable accuracy. This variant thus offers the advantage of an adjustment made particularly easy.

In some cases, however, the deformations of the nail in the plane X-Y cause a displacement of the distal hole along a circular trajectory with a rotational center close to the proximal extremity of the nail 1 or of the rotational point of the hip. The distal hole thus moves mainly along the axis Y but also, with a lesser amplitude, along the axis X. In a variant of this first embodiment, the regulating element thus allows the extremity of the viewing device to be displaced along a trajectory comprising a main component in Y and, simultaneously, in a dependent manner, along a lesser component in X, in order to follow the displacements of the distal hole. The movement remains a translational movement; the orientation of the viewing device is not modified. The two components in Y and in X are connected; there is thus only a single degree of freedom to position the viewing device along a curved trajectory in the plane X-Y.

In a preferred embodiment, in order to achieve these simultaneous and dependent movements in X and Y, the knob 7 actuates for example a glider moving in a guide or a slide defining the desired trajectory. The adjustment occurs by means of the knob 7 by acting according to a single degree of freedom to displace the viewing device in Y, possibly with a dependent component in X. The adjustment is thus very quick. The compensation in X is even more efficient if the curvature radius of the nail's deformation is known; it would be possible to conceive interchangeable gliders, for example one-way gliders, enabling the compensation in X to be adapted to the length of the nail.

The longitudinal adjustment along the axis Y is efficient even if the magnet pivots in the bone; it is only necessary for the longitudinal position of the magnet to correspond to the position of the distal hole. The magnet can thus be perfectly mounted at the extremity of a flexible rod with a cylindrical axis, free to rotate in the hole; the field lines 15 of the magnet, even isotropic, will be sufficient to position the viewing device 9 along the axis Y.

After the positioning of the viewing axis has been performed, it is possible to begin a step of drilling. For this purpose, the rod and the magnet are first withdrawn from the longitudinal channel in the nail, the viewing device 9 is then replaced on the rigid support 3 by a drill (not represented) or another tool.

Figure 2:
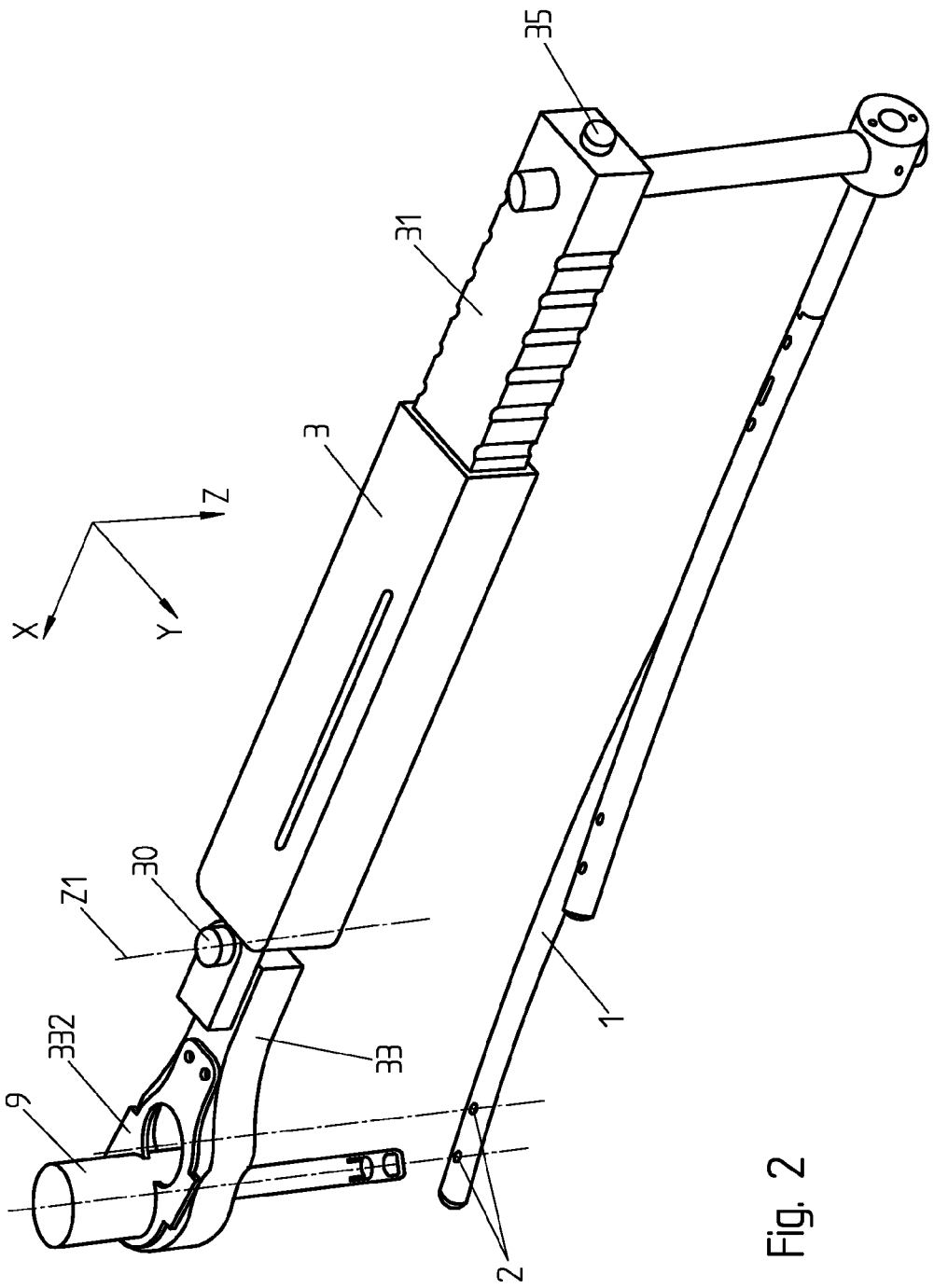
FIG. 2 illustrates in perspective a device according to a second embodiment of the invention.
Figure 3:
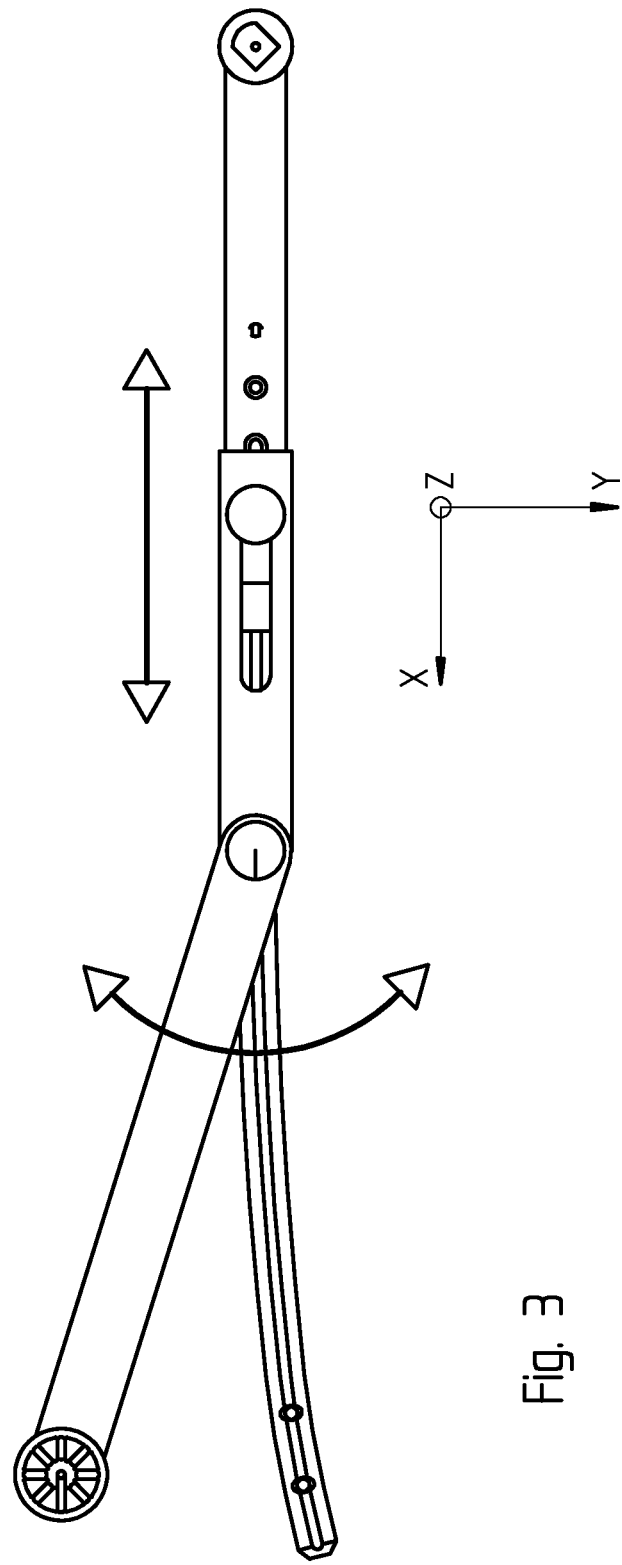
FIG. 3 is a view from above of a device according to the second embodiment of the invention.

FIG. 2 illustrates in perspective a device according to a second embodiment of the invention wherein the adjustment of the position of the viewing device 9 is made essentially by a rotational movement around an axis Z1 parallel to the viewing and drilling axis /. The device comprises a rigid support 3, for example of carbon fiber, telescopic with an extension portion 31 that makes it possible to coarsely adapt the length of the support along the axis X depending on the length of the nail 1; the adjustment is done advantageously in successive increments, for example in increments spaced by 20 mm or adapted to the available range of length of nails. A scale on the inner tube 31 can be displayed in a window, not represented, in the outer tube 3 in order to indicate the length currently selected. Holding is advantageously achieved by elastic deformation (clipsing) of the increments of the telescopic portion. In another variant illustrated on the FIG. 3, the indexing of the extension length of the telescopic tubes is achieved by means of a pin inserted in a pair of holes traversing both tubes.

A regulating screw 35 enables the distance of the nail 1 in Z to be adjusted relative to the support 3, depending on the patient's build. As for the incremental adjustment, this coarse adjustment is performed a priory, independently of the indications in the viewing device 9.

The distal extremity 33 of the support 3 is articulated relative to the body 3 of this support by means of a pivot 30; it can also pivot around the axis Z1 parallel to the viewing and drilling axis Z. In this embodiment, the adjustment is thus done in the plane perpendicular to the axis Z of the hole 2, but through a rotational rather than a translational movement. This adjustment option is illustrated in the top view of FIG. 3.

As in the variant of FIG. 1, the viewing device is disassembled and replaced by a drill or another tool when the optimum drilling position has been found.

Figure 4:
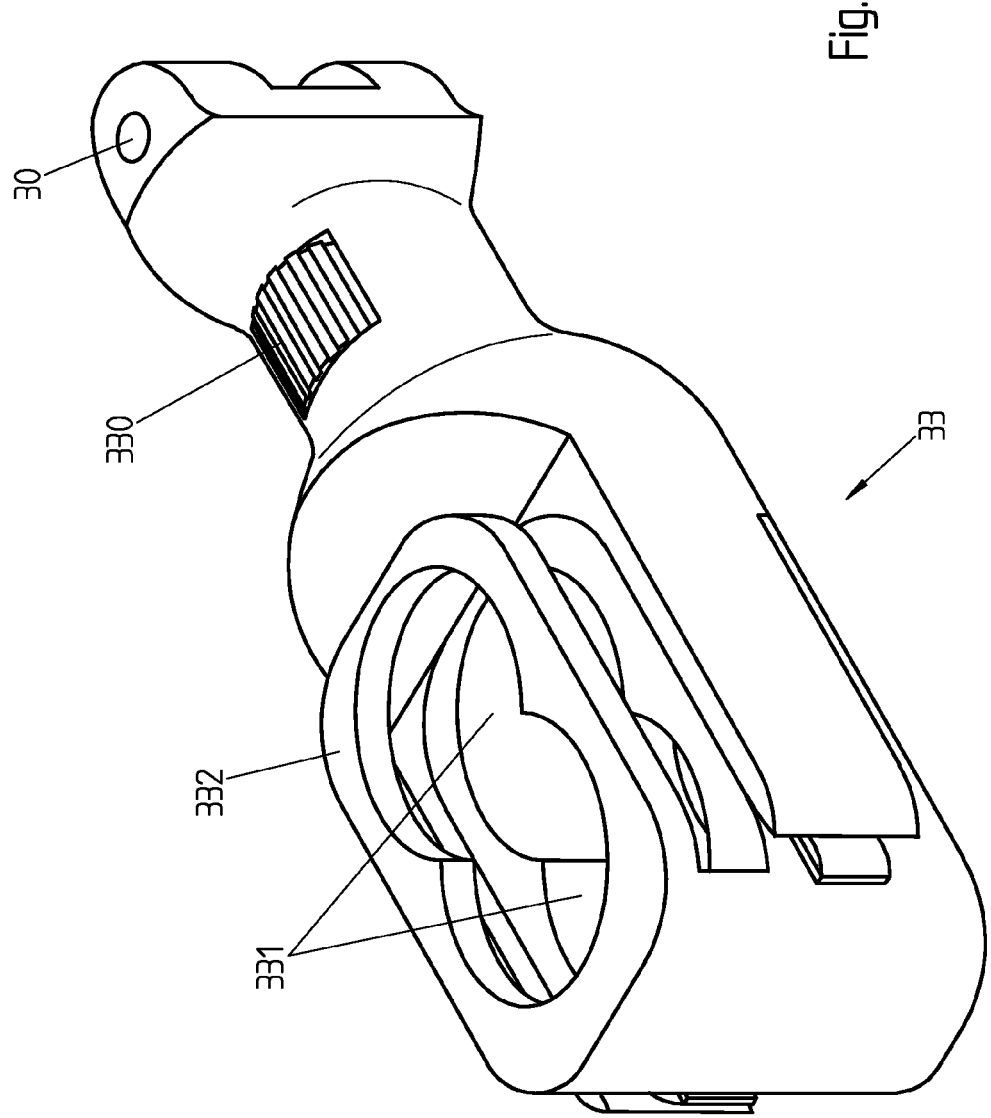
FIG. 4 is a perspective view of one of the parts of the device according to the second embodiment of the invention.

FIG. 4 illustrates in perspective an advantageous embodiment of the distal extremity 33 of the rigid support 3. In this variant, the length of the support 3 can be adjusted in a precise or fine manner along X by means of the micrometric screw which enables the element to be extended or shortened, in order to perform a precise correction and an adjustment of the position of the viewing device along the axis X. Reference number 331 indicates the hole in which the viewing device, and then the drill, are inserted and held. The hole advantageously comprises two predefined locations allowing the viewing device or the drill to be mounted at two different places, for example to drill opposite the two holes of the distal extremity of the nail. Reference number 332 corresponds to a lever enabling the viewing device 9 and subsequently the drill to be held in the hole 331.

FIGS. 5 and 6 illustrate a cross-sectional view of an example of viewing device 9 according to the invention. It comprises a conical shell 97 advantageously made of molded or injected synthetic material, for example homo-polymer. The axis of the shell determines the viewing axis (Z). One of the extremities of the shell is closed by a glass or a viewing surface of transparent plastic material clipsed in the shell; this viewing surface enables the surgeon to observe through it the position of a pointer 92 fastened to the extremity of a rod 91 and indicating the adjustment that needs to be done to bring the viewing device opposite the magnet in the nail. The rod 91 is advantageously made of carbon or any other non-magnetic material. The pointer 92 can be executed for example by means of a heat-shrinkable sheathing fastened onto the rod, for example a sheathing in a bright color.

The rod 91 is articulated on a bearing 93 clipsed in the viewing device 9. The other extremity of the rod is provided with a magnet 94 whose position is influenced by the magnetic field 15 emitted by the magnet in the nail 2. The reference numbers 95 designate bushings threaded on the rod 91 on both sides of the bearing and that constitute stops to prevent the sliding of this rod relative to the bearing, without preventing it from pivoting. The pivoting point can for example consist of a simple hole in the bearing 93. The assembly of parts forming the viewing device is preferably fastened to the shell 97 by clipsing or elastic deformation.

When the pivoting magnet 94 is oriented towards the magnet in the nail, the pointer 92 at the extremity of the rod 91 opposite the bone moves in the lens of the viewing device 9 in a corresponding fashion. The lens comprises for example concentric circles on a transparent surface and thus draws a target in which the pointer 92 moves to indicate the position of the distal fixation hole 2. The adjustment of the knob 7, respectively of the pivot 30 and of the thumb wheel 330, causes a displacement of the viewing device 9 in the plane X-Y. The magnet 94 pivots to become oriented towards the nail's magnet, driving the pointer 92.

Figure 7:
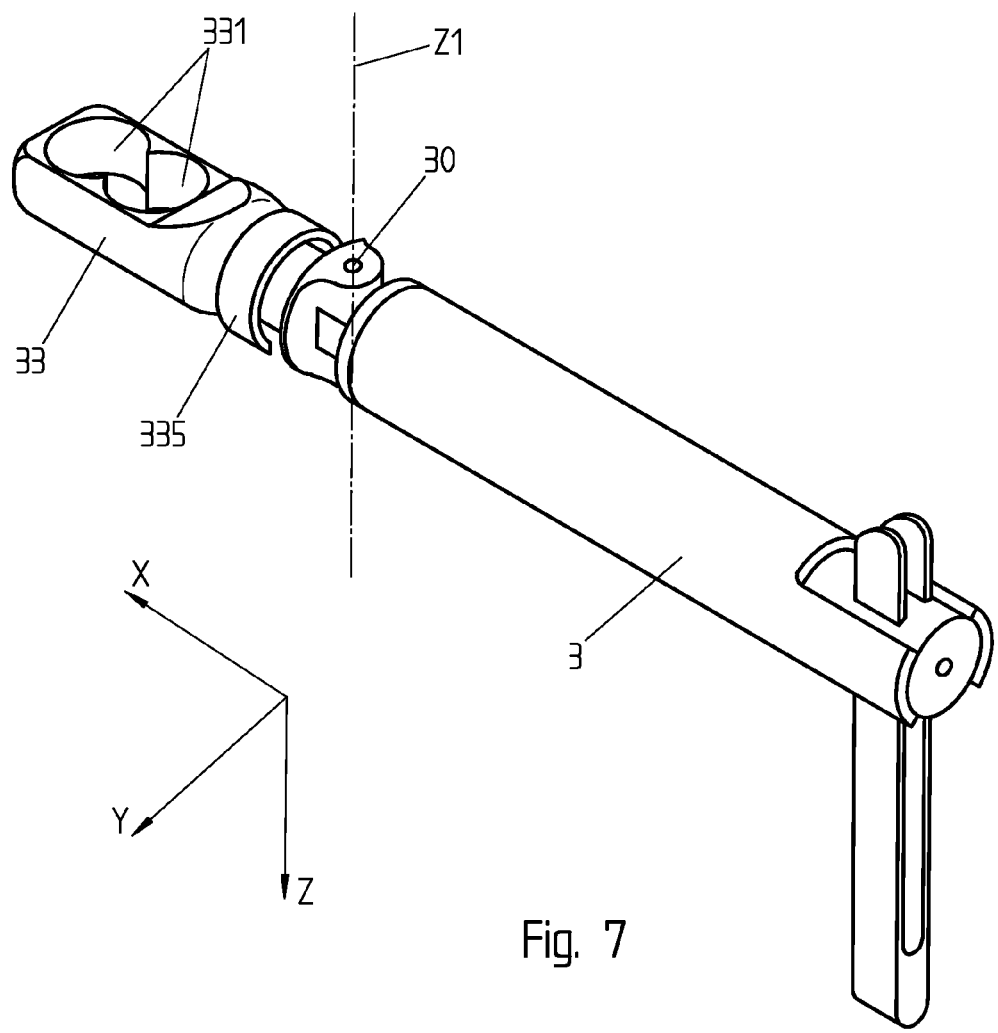
FIG. 7 is a view from above of a variant of the device according to the second embodiment of the invention.

FIG. 7 illustrates in perspective a second variant of the device according to the second embodiment. The possible movements of the viewing device, not represented, to be inserted in the lodging 331 of the distal extremity 33 are the same as in the first variant described here above in relation with FIGS. 2 to 6; the viewing device can also pivot around the axis Z1 parallel to the viewing and drilling axis Z, by means of a pivot 30. A ring 335 can be loosened to modify the length of the distal extremity 33 and then tightened again to lock the chosen position.

Figure 8:
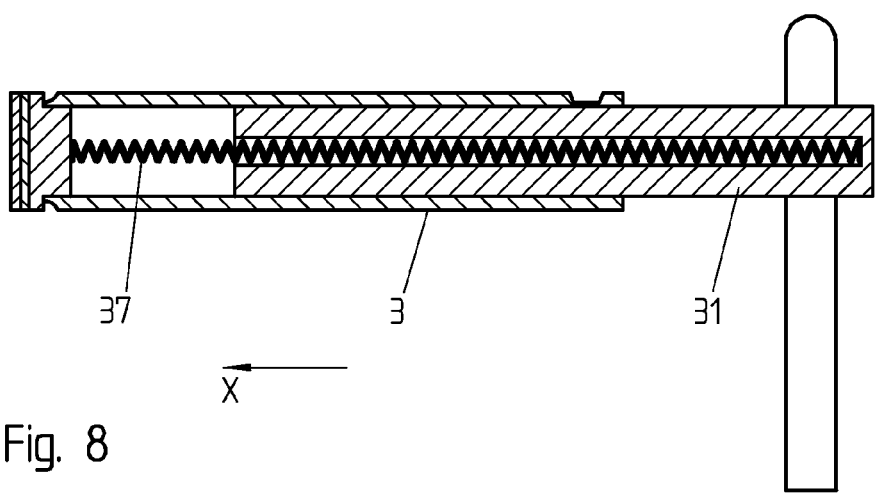
FIG. 8 is a cross-sectional view of a detail of a variant of the device according to the second embodiment of the invention.

This variant is distinguished from the first variant here above mainly by the body 3 of the rigid support, which is formed here of a telescopic tube having a cylindrical cross-section. A longitudinal spring 37 (FIG. 8) is lodged and constantly compressed inside an inner tube 31 in order to make the telescopic assembly more rigid and ensure accuracy of positioning at each indexation position of the tubes. The adaptation of the length of the tube 3 to the length of the nail is advantageously achieved by means of a pin connected to the outer tube and which follows a slit through the inner tube comprising several stop positions every 20 millimeters for example.

The device can also be adapted for fitting all centromedullary nails having a longitudinal guiding channel as well as for fitting channel-less nails, including fitting long prostheses. In particular, the device can be adapted for fitting flat nails without cavities integrating a magnet in the nail's mass or extender nails. IN this case, the hole through the nail is generally not drilled but its location is planned in advance; the drilling of the nail is done with the drilling of the bone, at this location and in a direction perpendicular to the surface of the nail. The device enables in this case the positioning of the viewing axis relative to the distal fixation hole provided in the intramedullary nail. If the magnet is mounted in the nail's mass at a distance from the location planned for drilling, it will be necessary to mount the drill on the support at a distance of the location detected with the viewing device. The magnet can also be clipsed in a hole of the nail and withdrawn before or during drilling.

This device proves particularly adapted to diminish the operating costs and simplify the operational mode thanks to the use of parts that are inexpensive, easy to machine and modular. The modularity of the parts, for example for the viewing and drilling sequences, makes it possible to clean and sterilize more easily the different parts when they are used separately than in the case of a device where it is impossible to disunite the constitutive parts of the device, notably those intended for viewing and those intended for drilling. Most of the parts that are re-used, notably the rigid support 3 and possibly the rod with the magnet, can thus be designed with a cylindrical section enabling them to be sterilized efficiently. The other parts, notably the viewing device 9 and the sleeve 14, are preferably disposable.

The use of a disposable viewing device 9 and/or sleeve 14, constituted only of mechanical parts, is independent of the displacements of the viewing device 9 limited along the axis Z.

The invention claimed is:

1. Device for positioning a viewing axis in relation to a distal fixation hole for an intramedullary nail, said device comprising a viewing device and a rigid support,
    wherein said viewing device comprises a longitudinal axis;
    wherein said rigid support ensures the positioning of said viewing device in relation to the intramedullary nail,
    wherein the position of the viewing device is adjustable depending on indications in said viewing device by displacing said viewing device in a plane perpendicular to its said longitudinal axis;
    wherein the viewing device further comprises a magnet pivoting relative to the support and working together with a magnet lodged in said nail, said pivoting magnet being connected to a rod pivoting around a fixed point of the viewing device, wherein the extremity of the rod opposite to said pivoting magnet is provided with a pointer.

2. The device of claim 1, wherein the position of the viewing device is adjustable depending on indications in said viewing device by translational and/or rotational movements in said plane perpendicular to its said longitudinal plane.

3. The device of claim 2, wherein the position of the viewing device is adjustable depending on indications in said viewing device only by translational movements along a single axis in said plane perpendicular to its said longitudinal plane.

4. The device of claim 3, wherein the position of the viewing device is adjustable depending on the indications in said viewing device only by translational movements along an axis perpendicular to said nail.

5. The device of claim 2, wherein the position of the viewing device is adjustable depending on indications in said viewing device rotational movements in said plane perpendicular to its said longitudinal axis.

6. The device of claim 5, wherein said device is arranged to allow said rotational movements to be performed along an axis connected to the rigid support and parallel to said longitudinal axis of the viewing device.

7. The device of claim 6, comprising a pivot enabling the distal extremity to pivot relative to said rigid support.

8. The device of claim 2, wherein the position of the viewing device is adjustable depending on indications in said viewing device rotational movements in said plane perpendicular to said longitudinal axis of the viewing device and by translational movements along an axis parallel to said nail.

9. The device of claim 8, wherein said device is arranged to allow all said rotational movements to be performed along an axis parallel to said longitudinal axis of the viewing device.

10. The device of claim 9, comprising a pivot for orienting a distal extremity relative to said rigid support and a thumb wheel actuating a micrometric screw to adjust in a continuous fashion the length of said fixed support.

11. The device of claim 1, arranged to enable translational movements of said viewing device along its said longitudinal axis in order to move it closer to the nail, taking account of a patient's build.

12. The device of claim 11, wherein said displacements of the viewing device along its longitudinal axis do not influence the indications displayed by the viewing device.

13. Device according to claim 1, whose parts comprise exclusively mechanical and/or magnetic parts.

14. Device according to claim 1, said viewing device comprising:

a shell of synthetic material;

a bearing inserted into said shell and holding said rod;

a viewing surface inserted into said shell.

15. Device according to claim 1, wherein said rigid support comprises a shape-keyed connection working with said nail to determine a viewing axis parallel to the one of said distal fixation hole.

16. Device according to claim 1, wherein the length of said rigid support is adjustable by increments by adding an additional removable assembly part to work with nails of different lengths.

17. Device according to claim 1, said rigid support being formed of telescopic elements whose length is adjustable by increments to work with nails of different lengths.

* * * * *